(12) United States Patent
Rheinberger et al.

(10) Patent No.: US 8,691,122 B2
(45) Date of Patent: Apr. 8, 2014

(54) MULTI-COLORED SHAPED BODY

(75) Inventors: Volker M. Rheinberger, Vaduz (LI); Marcel Schweiger, Chur (CH); Robert Kruse, Feldkirch (AT); Harald Kerschbaumer, Klaus (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 13/155,124

(22) Filed: Jun. 7, 2011

(65) Prior Publication Data

US 2011/0236857 A1    Sep. 29, 2011

Related U.S. Application Data

(63) Continuation of application No. 11/819,412, filed on Jun. 27, 2007, now Pat. No. 7,981,531.

(30) Foreign Application Priority Data

Sep. 13, 2006 (EP) .................... 06120608

(51) Int. Cl.
*A61C 13/00* (2006.01)

(52) U.S. Cl.
USPC .......................................... 264/20

(58) Field of Classification Search
CPC .................. A61C 13/0004; A61C 13/0022
USPC ....................................... 264/20
See application file for complete search history.

(56) References Cited

U.S. PATENT DOCUMENTS

| | | | |
|---|---|---|---|
| 3,148,981 A * | 9/1964 | Ryshkewitch | ............... 264/642 |
| 4,104,798 A | 8/1978 | Takahashi et al. | |
| 4,433,959 A | 2/1984 | Faunce | |
| 4,451,236 A | 5/1984 | Tarasov et al. | |
| 4,742,030 A | 5/1988 | Masaki et al. | |
| 4,751,099 A | 6/1988 | Niino et al. | |
| 4,778,649 A | 10/1988 | Niino et al. | |
| 4,970,032 A | 11/1990 | Rotsaert | |
| 4,997,723 A | 3/1991 | Tanaka | |
| 5,011,403 A | 4/1991 | Sadoun et al. | |
| 5,076,789 A | 12/1991 | Tanaka | |
| 5,151,044 A | 9/1992 | Rotsaert | |
| 5,263,858 A | 11/1993 | Yoshida et al. | |
| 5,308,243 A | 5/1994 | Emmons | |
| 5,455,000 A | 10/1995 | Seyferth et al. | |
| 5,532,057 A | 7/1996 | Jones | |
| 5,593,305 A | 1/1997 | Shoher et al. | |
| 5,656,564 A | 8/1997 | Nakayama et al. | |
| 5,730,600 A | 3/1998 | Shoher et al. | |
| 5,780,171 A | 7/1998 | Nissley et al. | |
| 5,800,164 A | 9/1998 | Pfau | |
| 6,171,572 B1 | 1/2001 | Aozasa et al. | |
| 6,379,593 B1 | 4/2002 | Datzmann et al. | |
| 6,495,072 B1 | 12/2002 | Van der Zel et al. | |
| 6,618,717 B1 | 9/2003 | Karadimitriou et al. | |
| 6,713,421 B1 | 3/2004 | Hauptmann et al. | |
| 7,686,989 B2 | 3/2010 | Van der Zel et al. | |
| 2002/0136658 A1 | 9/2002 | Dilmore et al. | |
| 2003/0125189 A1 | 7/2003 | Castro et al. | |
| 2004/0152034 A1 | 8/2004 | Cummings et al. | |
| 2005/0117146 A1 * | 6/2005 | Jung et al. | ............... 356/72 |
| 2007/0082229 A1 | 4/2007 | Mirchandani et al. | |
| 2007/0141367 A1 | 6/2007 | Darolia et al. | |
| 2007/0292597 A1 | 12/2007 | Ritzberger et al. | |
| 2008/0303181 A1 | 12/2008 | Holand et al. | |

FOREIGN PATENT DOCUMENTS

| | | |
|---|---|---|
| DE | 19944130 | 4/2001 |
| EP | 1076036 A1 | 2/2001 |
| EP | 1354567 | 10/2003 |
| EP | 1400232 | 3/2004 |
| FR | 2781366 A1 | 1/2000 |
| JP | 05068687 | 3/1993 |
| JP | 8033650 A | 2/1996 |
| JP | 2003321316 | 11/2003 |
| JP | 2004035332 | 2/2004 |
| WO | 2007053084 | 5/2007 |

* cited by examiner

*Primary Examiner* — Yogendra Gupta
*Assistant Examiner* — Alison Hindenlang
(74) *Attorney, Agent, or Firm* — Ann M. Knab; Thad McMurray

(57) ABSTRACT

The present invention relates to a multi-colored shaped body having layers arranged on top of one another for producing dental restorations, a process for its production and its use for the manufacture of dental restorations.

34 Claims, No Drawings

MULTI-COLORED SHAPED BODY

CROSS-REFERENCE TO RELATED APPLICATIONS

This application is a continuation of U.S. application Ser. No. 11/819,412, filed Jun. 27, 2007, which claims priority pursuant to 35 U.S.C. §119, to European Patent Application No. 06120608.2 filed Sep. 13, 2006, all of which are incorporated herein by reference.

FIELD OF THE INVENTION

The invention relates to a multi-colored shaped body having layers arranged on top of one another, which is suitable for manufacturing dental restorations and in which the change of color between the individual layers cannot be perceived without technical aids.

BACKGROUND OF THE INVENTION

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

Dental restoration parts can be manufactured from ceramic or plastic shaped bodies. This procedure is usually mechanical, for example, computer-aided according to a CAD/CAM method. With regard to the final use of the dental restoration parts, the shaped bodies should already have certain aesthetic properties.

Natural teeth are not one-colored, but have a complex coloration. Different areas of the same tooth can differ from each other in color and transparency. In general, teeth exhibit a color and transparency gradient from transparent in the occlusal area to yellowish-opaque in the cervical area.

In order to achieve a desired coloration, dental restoration parts which have a single color can be subsequently veneered. However, such veneering usually has to be carried out manually, which is time-consuming. Multi-colored shaped bodies are therefore preferred from which dental restoration parts can be manufactured that satisfy aesthetic requirements without veneering and which have a coloration that comes as close as possible to natural teeth in terms of color and transparency, as well as color gradient.

Multi-colored shaped bodies which are built up from several differently colored layers are known from the state of the art.

Thus, VITA Zahnfabrik GmbH offers VITABLOCS® Triluxe, which consist of three differently colored layers of a feldspar ceramic and are intended to simplify the manufacture of optically attractive dental restoration parts. These restoration parts are, however, still veneered.

U.S. Pat. No. 5,151,044 describes multi-layered blocks made from plastic materials which can be used for the manufacture of artificial teeth or denture parts. These blocks preferably contain up to three differently colored layers in order to simulate the color gradient of natural teeth.

Furthermore, it is known from DE 199 44 130 A1 to use blocks comprising several differently colored layers with standardized optical properties for the manufacture of denture parts by means of CAD/CAM methods. In doing so, the virtual positioning of the restoration part within a block is optimized such that the color gradient of what later becomes the restoration part comes as close as possible to a corresponding natural tooth of the patient. Veneering of the restoration parts produced in this way is said to be dispensable.

However, in the case of the multi-colored shaped bodies which are built up of differently colored layers, the color boundaries between the individual layers are clearly perceptible. Therefore the restoration parts produced according to the state of the art must be veneered as previously mentioned in order to achieve a restoration satisfying high aesthetic requirements.

DE 197 14 178 A1 describes a process for manufacturing a multi-colored shaped body wherein the color boundaries between the individual layers are said not to be perceptible. According to this, the contact surfaces of the individual layers are subjected to pressure and the differently colored starting materials are brought into intimate contact in the boundary area to allow for a mixing of the starting materials.

However, practice has shown that this process does not lead to an adequate mixing and therefore the boundaries between the colored layers in the thus-produced shaped bodies and restoration parts remain perceptible to the naked eye.

There is therefore a need for a multi-colored shaped body for producing dental restorations with differently colored layers in which no color boundaries can be seen with the naked eye between the individual layers.

SUMMARY OF THE INVENTION

The invention optionally addresses one or more of the above-mentioned shortcomings associated with the state of the art.

According to one aspect, the present invention provides a multicolored shaped body having layers arranged on top of one another comprising: at least two successive and differently colored main layers; and at least two differently colored intermediate layers between the at least two successive and differently colored main layers; wherein a change in color between these intermediate layers takes place in a direction which is contrary to the direction of the change in color between the main layers.

According to another aspect, the present invention provides a multicolored shaped body having layers arranged on top of one another comprising: at least two successive and differently colored main layers; and an intermediate layer between at least two successive and differently colored main layers; wherein the intermediate layer comprises a mixture of the materials of the two successive main layers.

According to a further aspect, the present invention provides dental articles and processes related to the above-described multi-colored shaped bodies.

The terms "color" and "colored" within the meaning of the invention relate to the color, brightness and translucency of a material, body or layer. According to the invention the terms "color" and "colored" relate in particular to brightness. Changes in color are therefore understood to include in particular changes in brightness.

"Translucency" is the light-transmitting capacity of a material, body or layer, i.e., the ratio of transmitted to incident light intensity.

Colors can for example also be characterized by their Lab value or by a color code common in the dental industry. Examples of such color codes are the Vitapan Classical® and the Vita 3D Master®, both from VITA Zahnfabrik H. Rauter GmbH & Co. KG, and Ivoclar Vivadent AG's Chromascop®.

Measurements of layer thicknesses can for example be made on cross-sections from a shaped body taken vertically with respect to the layering and polished, by recording scaled microscopic images of these sections with a stereoscope and carrying out length measurements on these photographs, e.g., with the analySIS Five image-processing software. In particular, layer thickness means the average of several thicknesses determined for a layer.

DETAILED DESCRIPTION OF THE INVENTION

A multi-colored shaped body according to the invention having layers arranged on top of one another can comprise: at least two successive and differently colored main layers; and
at least two differently colored intermediate layers between at least two successive and differently colored main layers; wherein a change in color between these intermediate layers takes place in a direction which is contrary to the direction of the change in color between the main layers.

The change in colors can essentially be a change in their respective brightness. In one embodiment the change of brightness in the intermediate layers takes place in a direction which is contrary to the direction of the change in brightness between the main layers.

It has surprisingly been shown that shaped bodies formed and structured according to the invention have color boundaries between differently colored main layers that are practically imperceptible to the naked eye.

It has also been recognized that the clear perceptibility of the color boundaries between individual layers in previously known shaped bodies is enhanced by an optical illusion.

When observing neighboring surfaces differing in color or brightness, so-called lateral inhibition of neighboring receptors in the retina occurs in the human eye. Therefore, in the boundary area of two differently colored surfaces the dark surface appears darker than in areas more distant from the boundary area, but the bright area appears brighter than in areas further away from the boundary area. The higher-contrast changes perceived by the human eye are called Mach bands. By this effect the contrast at the color boundary is increased and the perception of the color boundary enhanced. Because of this effect, in a series of differently colored layers each of which is one-colored in itself, within the individual layers a color gradient is perceived which is contrary to the gradient of the colors of the individual layers. These effects are more strongly perceived with brighter colors than with darker colors.

The described optical effects are contrary to the desired aim of dental restorations to achieve a natural color gradient. Thus, the color gradient of known multi-colored shaped bodies has boundaries between the layers that are clearly perceptible. The shaped bodies according to the invention compensate or even over-compensate for these effects by the insertion of specially developed intermediate layers. A color gradient is achieved thereby in which the boundaries of the differently colored layers are no longer perceptible to the naked eye.

The subject of one embodiment of the invention is a multi-colored shaped body wherein the intermediate layers lying between two successive and differently colored main layers alternately have the colors of these main layers. A desired color gradient in which the color boundaries are practically imperceptible can thereby be achieved using relatively few colors.

Another embodiment comprises a multi-colored shaped body wherein, between two successive and differently colored main layers, precisely two intermediate layers are arranged and each of these intermediate layers has the color of the main layer which is adjacent to the respective other intermediate layer.

Accordingly, such a shaped body is also preferred which has at
least one element of four layers arranged on top of one another, wherein
the first layer is a first main layer;
the second layer is an intermediate layer having the color of a second main layer;
the third layer is an intermediate layer having the color of the first main layer;
the fourth layer is the second main layer.

With shaped bodies according to the invention the total number of main and intermediate layers is at least four, i.e., there are at least two main layers and at least two intermediate layers. The shaped bodies according to the invention may have 4 to 20, in particular 4 to 10 and more particularly 4 to 8 main and intermediate layers.

The increase in contrast which occurs at the boundaries of the main layers in the absence of intermediate layers is pronounced to a greater or lesser degree, depending on the translucency and brightness of the layers involved. With shaped bodies with more than two main layers, it is therefore not absolutely necessary to insert intermediate layers at every boundary between two main layers. Thus a dental restoration which satisfies high aesthetic requirements can be manufactured from a shaped body which can be produced economically.

In an alternative embodiment a shaped body according to the invention has eight layers arranged on top of one another, wherein
(a) the first layer is a first main layer;
(b) the second layer is a second main layer;
(c) the third layer is an intermediate layer having the color of a third main layer;
(d) the fourth layer is an intermediate layer having the color of the second main layer;
(d) the fifth layer is the third main layer;
(e) the sixth layer is an intermediate layer having the color of a fourth main layer;
(f) the seventh layer is an intermediate layer having the color of the third main layer; and
(g) the eighth layer is the fourth main layer.

A shaped body according to the invention may have a height of 10 mm to 20 mm, more particularly 14 mm to 16 mm.

The main layers of the shaped body according to the invention may have a thickness of more than 0.5 mm, in particular more than 0.5 mm and up to 15 mm, more than 0.5 mm and up to 10 mm, and still more particularly 0.7 mm to 8 mm.

The intermediate layers of the shaped body according to the invention may have a thickness of up to 0.5 mm, in particular 0.01 mm to 0.5 mm, more particularly 0.1 mm to 0.5 mm, and still more particularly 0.2 mm to 0.4 mm.

A shaped body according to the invention can be formed of any material suitable for producing shaped bodies for dental restorations. Such materials include ceramics, glass ceramics, plastics, inorganic-organic composites or mixtures thereof.

A shaped body, according to one embodiment, contains (a) $SiO_2$, (b) $Al_2O_3$ and (c) $K_2O$ and/or $Na_2O$. A shaped body according to another embodiment is made from $Al_2O_3$ and/or $ZrO_2$ ceramic material.

Differently colored layers can be of the same material which is differently colored in each case, or can be formed of different materials.

The layering of the shaped bodies is can be based on the layering of the color codes common in the dental industry, such as the Vitapan Classical® or the Vita 3D Master®, both from VITA Zahnfabrik H. Rauter GmbH & Co. KG, or Ivoclar Vivadent AG's Chromascop®. The tooth models of these color codes in each case define only one color, but similar to teeth are built up of layers of different material mixtures and/or colors and/or translucencies, and are based on the different colors of human teeth. This basic color allocation is preferably also used in the shaped bodies according to the invention, with the result that the dental restorations produced from them correspond very closely to the natural tooth.

According to a further embodiment of the invention a multi-colored shaped body for producing dental restorations may comprise
at least two successive and differently colored main layers and
an intermediate layer between at least two successive and differently colored main layers,
wherein the intermediate layer comprises a mixture of the materials of the two successive main layers, and may optionally consist thereof.

The main layers of this other shaped body according to the invention preferably have a thickness of more than 0.5 mm, in particular more than 0.5 mm and up to 15 mm, more than 0.5 mm and up to 10 mm, and still more particularly 0.7 mm to 8 mm.

The intermediate layer of this other shaped body according to the invention may have a thickness of up to 0.5 mm, in particular 0.01 mm to 0.5 mm, particularly 0.1 mm to 0.5 mm, and more particularly 0.2 mm to 0.4 mm.

Further embodiments of the invention have the properties with respect to preferred numbers of layers, preferred heights of the shaped body and preferred materials as described above for the other embodiments.

The invention also relates to a process for manufacturing the multicolored shaped bodies according to the invention having layers arranged on top of one an other, in which the main layers and intermediate layers are arranged on top of one another such that a shaped body according to the invention is obtained.

Finally the invention also relates to the use of the multicolored shaped bodies according to the invention for the manufacture of dental restorations. The manufacture of dental restorations can be computer-aided, in particular by means of CAD/CAM methods. Preferred dental restorations are artificial teeth, inlays, onlays, bridges and crowns.

The invention is explained in more detail below with reference to the following illustrative, non-limiting examples.

Example 1

Two Intermediate Layers

For the manufacture of a multi-colored shaped body having differently colored layers, the following materials (glass ceramic powders) are used:

| | |
|---|---|
| SiO2: | 60.0-65.0% |
| Al2O3: | 16.0-20.0% |
| K2O: | 10.0-14.0% |
| Na2O: | 3.5-6.5% |
| B2O3: | 0-1.0% |
| BaO: | 0-1.5% |
| CaO: | 0.5-2.5% |
| CeO2: | 0-1.0% |
| TiO2: | 0-0.5% |
| F: | 0-0.5% |
| Pigments: | 0.2-1.0% |

By appropriate pigment addition, the colorings M1 and M2 of the glass ceramic material are produced, wherein M1, for example, corresponds to the dentine color A2 according to Vitapan Classical® and has a high opacity. M2 corresponds to an incisor color and has a lower opacity. By different mixing of the materials M1 and M2 four differently colored material compositions A to D result, which are composed as follows:

| | |
|---|---|
| Material A: | 100% M1 |
| Material B: | 2/3 M1, 1/3 M2 |
| Material C: | 1/3 M1, 2/3 M2 |
| Material D: | 100% M2 |

The individual materials are introduced gradually in a customary form of a compression mold so that the following series of layers results:

| | |
|---|---|
| 1st layer: | 6th layer: |
| 2nd layer: | 7th layer: |
| 3rd layer: | 8th layer: |
| 4th layer: | 9th layer: |
| 5th layer: | 10th layer: |

| | |
|---|---|
| main layer, material A | material B |
| intermediate layer, material B | intermediate layer, material C |
| intermediate layer, material B | |
| intermediate layer, material A | main layer, material C |
| main layer, | intermediate layer, material D |
| | intermediate layer, material C |
| | main layer, material D |

After filling the compression mold with the individual layers the green body is produced in known manner by dry pressing, and then a processable shaped body with an overall height of approximately 10 to 15 mm is produced by debindering and sintering. This shaped body may optionally be subjected to further processing.

In the resulting shaped body the intermediate layers have a layer thickness of about 0.2 to about 0.4 mm. With this shaped body, and in a dental restoration produced from it, the changes between the individual layers are surprisingly imperceptible to the naked eye.

Example 2

Two Intermediate Layers

For the manufacture of a multi-colored shaped body having fundamentally differently colored layers, the following materials (glass ceramic powders) are used:

| | |
|---|---|
| $SiO_2$: | 60.0-65.0% |
| $Al_2O_3$: | 16.0-20.0% |
| $K_2O$: | 10.0-14.0% |
| $Na_2O$: | 3.5-6.5% |
| $B_2O_3$: | 0-1.0% |
| BaO: | 0-1.5% |
| CaO: | 0.5-2.5% |

| | |
|---|---|
| CeO$_2$: | 0-1.0% |
| TiO$_2$: | 0-0.5% |
| F: | 0-0.5% |
| Pigments: | 0.2-1.0% |

By appropriate pigment addition, the colorings M1 and M2 of the glass ceramic material are produced, wherein M1, for example, corresponds to the dentine color A2 according to Vitapan Classical® and has a high opacity. M2 corresponds to an incisor color and has a lower opacity. By different mixing of the materials M1 and M2 four differently colored material compositions A to D result, and from these in turn six differently colored materials of the intermediate layers AB1, AB2, BC1, BC2, CD1, CD2:

| | |
|---|---|
| Material A: | 100% M1 |
| Material B: | 2/3 M1, 1/3 M2 |
| Material C: | 1/3 M1, 2/3 M2 |
| Material D: | 100% M2 |

| | |
|---|---|
| Material AB1: | 1/3 A, 2/3 B |
| Material AB2: | 2/3 A, 1/3 B |
| Material BC1: | 1/3 B, 2/3 C |
| Material BC2: | 2/3 B, 1/3 C |
| Material CD1: | 1/3 C, 2/3 D |
| Material CD2: | 2/3 C, 1/3 D |

The individual materials are introduced gradually in a customary form of a compression mold so that the following series of layers results:

| | |
|---|---|
| 1$^{st}$ layer: | main layer, material A |
| 2$^{nd}$ layer: | intermediate layer, material AB1 |
| 3$^{rd}$ layer: | intermediate layer, material AB2 |
| 4$^{th}$ layer: | main layer, material B |
| 5$^{th}$ layer: | intermediate layer, material BC1 |
| 6$^{th}$ layer: | intermediate layer, material BC2 |
| 7$^{th}$ layer: | main layer, material C |
| 8$^{th}$ layer: | intermediate layer, material CD1 |
| 9$^{th}$ layer: | intermediate layer, material CD2 |
| 10$^{th}$ layer: | main layer, material D |

After filling the compression mold with the individual layers the green body is produced in known manner by dry pressing, and then processable shaped body with an overall height of approximately 10 to 15 mm is produced by debindering and sintering. This shaped body may optionally be subjected to further processing.

In the thus-obtained shaped body the intermediate layers have a layer thickness of approximately 0.2 to approximately 0.4 mm. With this shaped body and with a dental restoration produced from it, the changes between the individual layers are surprisingly imperceptible to the naked eye.

Example 3

One Intermediate Layer

For the manufacture of a multi-colored shaped body having differently colored layers, the following materials (glass ceramic powders) are used:

| | |
|---|---|
| SiO$_2$: | 60.0-65.0% |
| Al$_2$O$_3$: | 16.0-20.0% |
| K$_2$O: | 10.0-14.0% |
| Na$_2$O: | 3.5-6.5% |
| B$_2$O$_3$: | 0-1.0% |
| BaO: | 0-1.5% |
| CaO: | 0.5-2.5% |
| CeO$_2$: | 0-1.0% |
| TiO$_2$: | 0-0.5% |
| F: | 0-0.5% |
| Pigments: | 0.2-1.0% |

By appropriate pigment addition, the colorings M1 and M2 of the glass ceramic material are produced, wherein M1 for example corresponds to the dentine color A2 according to Vitapan Classical® and has a high opacity. M2 corresponds to an incisor color and has a lower opacity. By different mixing of the materials M1 and M2 four differently colored material compositions A to D result, and from these in turn three differently colored materials of the intermediate layers AB, BC, CD:

| | |
|---|---|
| Material A: | 100% M1 |
| Material B: | 2/3 M1, 1/3 M2 |
| Material C: | 1/3 M1, 2/3 M2 |
| Material D: | 100% M2 |
| Material AB: | 50% A, 50% B |
| Material BC: | 50% B, 50% C |
| Material CD: | 50% C, 50% D |

The individual materials are introduced gradually in a customary form of a compression mold so that the following series of layers results:
a compression mold so that the following series of layers results:

| | |
|---|---|
| 1$^{st}$ layer: | main layer, material A |
| 2$^{nd}$ layer: | intermediate layer, material AB |
| 3$^{rd}$ layer: | main layer, material B |
| 4$^{th}$ layer: | intermediate layer, material BC |
| 5$^{th}$ layer: | main layer, material C |
| 6$^{th}$ layer: | intermediate layer, material CD |
| 7$^{th}$ layer: | main layer, material D |

After filling the compression mold with the individual layers the green body is produced in known manner by dry pressing, and then a processable shaped body with an overall height of approximately 10 to 15 mm is produced by debindering and sintering. This shaped body may optionally be subjected to further processing.

In the thus-obtained shaped body the intermediate layers have a layer thickness of approximately 0.2 to approximately 0.4 mm. With this shaped body and with a dental restoration produced from it, the changes between the individual layers are surprisingly imperceptible to the naked eye.

All numbers expressing quantities or parameters used in the specification are to be understood as additionally being modified in all instances by the term "about". Notwithstanding that the numerical ranges and parameters set forth, the broad scope of the subject matter presented herein are approximations, the numerical values set forth are indicated as precisely as possible. For example, any numerical value may inherently contains certain errors, evidenced by the standard deviation associated with their respective measurement techniques, or round-off errors and inaccuracies.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. A process for the manufacture of a dental restoration, comprising
   (i) providing a multi-colored shaped body comprising:
   at least two successive and differently colored main layers, wherein the main layers have a thickness of more than about 0.5 mm; and
   at least two differently colored intermediate layers between the at least two successive and differently colored main layers, wherein the intermediate layers have a thickness of up to about 0.5 mm;
   wherein a change in color between the intermediate layers takes place in a direction which is contrary to the direction of the change in color between the main layers; and
   (ii) processing the shaped body by a CAD/CAM technique to obtain the dental restoration;
   wherein the shaped body is formed from ceramic, glass ceramic, inorganic-organic composite, plastic or mixtures thereof.

2. The process according to claim 1, wherein the change in colors is essentially a change in their respective brightness.

3. The process according to claim 2, wherein an increase in brightness between the intermediate layers takes place in a direction which is contrary to the direction of the increase in brightness between the main layers.

4. The process according to claim 1, wherein the intermediate layers lying between two successive and differently colored main layers alternately have the colors of the main layers.

5. The process according to claim 1, wherein between two successive and differently colored main layers two intermediate layers are arranged and each of these intermediate layers has the color of the main layer which is adjacent to the respective other intermediate layer.

6. The process according to claim 1, wherein the shaped body comprises at least one element of four layers arranged on top of one another, wherein
   (a) the first layer is a first main layer;
   (b) the second layer is an intermediate layer having the color of a second main layer;
   (c) the third layer is an intermediate layer having the color of the first main layer;
   (d) the fourth layer is the second main layer.

7. The process according to claim 1, wherein the shaped body comprises 4-20 main and intermediate layers.

8. The process according to claim 7, wherein the shaped body comprises 4-10 main and intermediate layers.

9. The process according to claim 8, wherein the shaped body comprises 4-8 main and intermediate layers.

10. The process according to claim 1, wherein the shaped body has eight layers arranged on top of one another, wherein
    (a) the first layer is a first main layer;
    (b) the second layer is a second main layer;
    (c) the third layer is an intermediate layer having the color of a third main layer;
    (d) the fourth layer is an intermediate layer having the color of the second main layer;
    (e) the fifth layer is the third main layer;
    (f) the sixth layer is an intermediate layer having the color of a fourth main layer;
    (g) the seventh layer is an intermediate layer having the color of the third main layer; and
    (h) the eighth layer is the fourth main layer.

11. The process according to claim 1, wherein the main layers have a thickness of about 0.5 mm-15 mm.

12. The process according to claim 11, wherein the main layers have a thickness of about 0.5 mm-10 mm.

13. The process according to claim 12, wherein the main layers have a thickness of about 0.7 mm-8 mm.

14. The process according to claim 1, wherein the intermediate layers have a thickness of about 0.01 mm-0.5 mm.

15. The process according to claim 14, wherein the intermediate layers have a thickness of about 0.1 mm-0.5 mm.

16. The process according to claim 15, wherein the intermediate layers have a thickness of about 0.2 mm-0.4 mm.

17. The process according to claim 1, wherein the shaped body comprises:
    (a) $SiO_2$;
    (b) $Al_2O_3$; and
    (c) $K_2O$ and/or $Na_2O$.

18. The process according to claim 1, wherein the shaped body comprises an $Al_2O_3$ and/or $ZrO_2$ ceramic material.

19. The process according to claim 1, wherein the dental restoration comprises artificial teeth, inlays, onlays, bridges or crowns.

20. A dental restoration manufactured by the process according to claim 1.

21. A process for the manufacture of a dental restoration, comprising:
    (i) providing a multi-colored shaped body comprising:
    at least two successive and differently colored main layers, wherein the main layers have a thickness of more than about 0.5 mm; and
    an intermediate layer between at least two successive and differently colored main layers, wherein the intermediate layer has a thickness of up to about 0.5 mm;
    wherein the intermediate layer comprises a mixture of the materials of the two successive main layers; and
    (ii) processing the shaped body by a CAD/CAM technique to obtain the dental restoration;
    wherein the shaped body is formed from ceramic, glass ceramic, inorganic-organic composite, plastic or mixtures thereof.

22. The process according to claim 21, wherein the shaped body comprises 4-20 main and intermediate layers.

23. The process according to claim 22, wherein the shaped body comprises 4-10 main and intermediate layers.

24. The process according to claim 23, wherein the shaped body comprises 4-8 main and intermediate layers.

25. The process according to claim 21, wherein the main layers have a thickness of about 0.5 mm-15 mm.

26. The process according to claim 25, wherein the main layers have a thickness of about 0.5 mm-10 mm.

27. The process according to claim 26, wherein the main layers have a thickness of about 0.7 mm-8 mm.

28. The process according to claim 21, wherein the intermediate layer has a thickness of about 0.01 mm-0.5 mm.

29. The process according to claim 28, wherein the intermediate layer has a thickness of about 0.1 mm-0.5 mm.

30. The process according to claim 29, wherein the intermediate layer has a thickness of about 0.2 mm-0.4 mm.

31. The process according to claim 21, wherein the shaped body comprises:
    (a) $SiO_2$;
    (b) $Al_2O_3$; and
    (c) $K_2O$ and/or $Na_2O$.

32. The process according to claim 21, wherein the shaped body comprises an $Al_2O_3$ and/or $ZrO_2$ ceramic material.

33. The process according to claim 21, wherein the dental restoration comprises artificial teeth, inlays, onlays, bridges or crowns.

34. A dental restoration manufactured by the process according to claim 21.

* * * * *